(12) United States Patent
Bristow (10) Patent No.: US 10,947,181 B2
(45) Date of Patent: Mar. 16, 2021

(54) CRYSTALLINE FORM OF TEFLUTHRIN, PROCESS FOR ITS PREPARATION AND USE THEREOF

(71) Applicant: JIANGSU ROTAM CHEMISTRY CO., LTD, Jiangsu (CN)

(72) Inventor: James Timothy Bristow, Chai Wan (HK)

(73) Assignee: JIANGSU ROTAM CHEMISTRY CO., LTD, Jiangsu (CN)

( * ) Notice: Subject to any disclaimer, the term of this patent is extended or adjusted under 35 U.S.C. 154(b) by 0 days.

(21) Appl. No.: 16/491,113

(22) PCT Filed: Nov. 28, 2017

(86) PCT No.: PCT/CN2017/113240
§ 371 (c)(1),
(2) Date: Sep. 4, 2019

(87) PCT Pub. No.: WO2018/218896
PCT Pub. Date: Dec. 6, 2018

(65) Prior Publication Data
US 2020/0010403 A1    Jan. 9, 2020

(30) Foreign Application Priority Data

May 30, 2017    (AU) ................................ 2017203635

(51) Int. Cl.
| | | |
|---|---|---|
| C07C 69/743 | (2006.01) |
| A01N 25/14 | (2006.01) |
| A01N 25/30 | (2006.01) |
| A01N 53/00 | (2006.01) |
| C07C 67/52 | (2006.01) |

(52) U.S. Cl.
CPC ............ C07C 69/743 (2013.01); A01N 25/14 (2013.01); A01N 25/30 (2013.01); A01N 53/00 (2013.01); C07C 67/52 (2013.01); *C07B 2200/13* (2013.01); *C07C 2601/02* (2017.05)

(58) Field of Classification Search
CPC ....... C07C 67/52; C07C 69/743; A01N 25/14; A01N 25/30; A01N 53/00
USPC .......................................................... 560/124
See application file for complete search history.

(56) References Cited

U.S. PATENT DOCUMENTS

| | | |
|---|---|---|
| 4,405,640 A | 9/1983 | Punja |
| 4,486,355 A | 12/1984 | Bentley et al. |

(Continued)

FOREIGN PATENT DOCUMENTS

| | | | |
|---|---|---|---|
| CN | 1494525 A | | 5/2004 |
| CN | 1760168 A | * | 4/2006 |

(Continued)

OTHER PUBLICATIONS

Transmittal of International Search Report and Written Opinion regarding Application No. PCT/CN2017/113240 dated Feb. 24, 2018.

*Primary Examiner* — Deborah D Carr
(74) *Attorney, Agent, or Firm* — Dickinson Wright PLLC (57) ABSTRACT

Provided are the crystalline form of tefluthrin of formula (I), the crystal preparation process, the analyses of the crystal through various analytical methods and using the crystal to prepare stable agrochemical formulation. Also provided is the use of various solvents towards the crystalline form preparation conditions.

27 Claims, 4 Drawing Sheets

(56) References Cited

U.S. PATENT DOCUMENTS

2004/0063993 A1 4/2004 Jones et al.
2011/0263889 A1 10/2011 Bowden et al.

FOREIGN PATENT DOCUMENTS

| CN | 1760168 A | 4/2006 |
| CN | 102026954 A | 4/2011 |

* cited by examiner

CRYSTALLINE FORM OF TEFLUTHRIN, PROCESS FOR ITS PREPARATION AND USE THEREOF

CROSS REFERENCE TO RELATED APPLICATIONS

This application is the national phase of International Application No. PCT/CN2017/113240, titled "NOVEL CRYSTALLINE FORM OF TEFLUTHRIN, PROCESS FOR ITS PREPARATION AND USE THEREOF", filed on Nov. 28, 2017, which claims the priority to Australian Patent Application No. 2017203635, filed on May 30, 2017, and titled with "A NOVEL CRYSTALLINE FORM OF TEFLUTHRIN, A PROCESS FOR ITS PREPARATION AND USE OF THE SAME", and the disclosures of which are hereby incorporated by reference.

FIELD

The present invention relates to a crystalline form of 2,3,5,6-tetrafluoro-4-methylbenzyl-(1RS,3RS)-3-[(Z)-2-chloro-3,3,3-trifluoroprop-1-enyl]-2,2-di methylcyclopropanecarboxylate (tefluthrin), to its preparation processes and to its use in agrochemical preparations.

BACKGROUND 2,3,5,6-tetrafluoro-4-methylbenzyl-(1 RS,3RS)-3-[(Z)-2-chloro-3,3,3-trifluoroprop-1-en yl]-2,2-dimethylcyclopropanecarboxylate (tefluthrin) is a pyrethroid insecticide with a broad-spectrum control. The activity of tefluthrin is by contact and ingestion and then, interferes with nerve impulse transmission by affecting the sodium channels through the endocrine or neuroendocrine function in vivo. In other words, it permeates the soil and penetrates the insect cuticle, disrupting nerve conductance and causing cessation of feeding and death and giving additional protection to the plant. Tefluthrin is used as a soil insecticide to control soil pests, particularly those of the orders Coleoptera, Lepitoptera and Diptera, including corn rootworms, cutworms, wireworms and white grubs in maize, sugar beet and other crops. However, tefluthrin is one of the most toxic pyrethroids, especially for aquatic organisms.

Tefluthrin has molecular formula of $C17H14ClF7O2$. Its chemical structure is:

(I)

The commercially available tefluthrin, which is usually manufactured by the process described in U.S. Pat. No. 4,405,640, which is incorporated herein by reference for all purposes, is present in amorphous state. It has been found that tefluthrin in amorphous state is very toxic to aquatic organisms and is not suitable for being used in an economical agricultural formulation. Therefore, there is a need to provide a novel form of tefluthrin with reduced toxicity.

SUMMARY

In an attempt to resolve some or all of the problems with the existing amorphous form of tefluthrin, a new and less toxic form of tefluthrin has been prepared.

In a first aspect, the present invention provides a crystalline form of 2,3,5,6-tetrafluoro-4-methylbenzyl-(1RS,3RS)-3-[(Z)-2-chloro-3,3,3-trifluoroprop-1-enyl]-2,2-di methylcyclopropanecarboxylate (tefluthrin), termed "crystalline modification I", exhibiting at least three of the following reflexes, in any combination, as 2θ±0.20 degree in an X-ray powder diffractogram (X-RPD) recorded using Cu—Kα radiation at 25° C.:

| | |
|---|---|
| 2θ=12.54±0.20 | (1) |
| 2θ=12.82±0.20 | (2) |
| 2θ=16.82±0.20 | (3) |
| 2θ=21.59±0.20 | (4) |
| 2θ=22.10±0.20 | (5) |
| 2θ=23.33±0.20 | (6) |
| 2θ=24.72±0.20 | (7) |
| 2θ=25.18±0.20 | (8) |
| 2θ=25.82±0.20 | (9) |
| 2θ=26.98±0.20 | (10) |
| 2θ=27.65±0.20 | (11) |
| 2θ=30.58±0.20 | (12) |
| 2θ=31.63±0.20 | (13). |

In an embodiment, the crystalline modification I of tefluthrin according to the first aspect of the invention, exhibits at least 3, 4, 5 or all of the following reflexes, in any combination, as 2θ±0.20 degree in an X-ray powder diffractogram recorded using Cu—Kα radiation at 25° C.:

| | |
|---|---|
| 2θ=12.54±0.2 | (1) |
| 2θ=12.82±0.2 | (2) |
| 2θ=16.82±0.2 | (3) |
| 2θ=24.72±0.2 | (7) |
| 2θ=25.18±0.2 | (8) |
| 2θ=31.63±0.2 | (13). |

In a second aspect, the present invention provides a crystalline modification I of tefluthrin optionally according to the first aspect of the invention, exhibiting an infrared (IR) with characteristic functional group vibration peaks at wavenumbers (cm$^{-1}$, ±0.2%) of 3082, 1733, 1655, 1486, 1385, 1362, 1276, 1115, 1162 and 1068 cm$^{-1}$.

In a third aspect, the present invention provides a crystalline modification I of tefluthrin, optionally according to the first or second aspect of the invention, exhibiting a melting point of 41° C. to 46° C., preferably 42° C. to 45° C., more preferably 44° C.

In a fourth aspect, the present invention provides a crystalline modification I of tefluthrin, optionally according to any one of the first to third aspects of the invention, exhibiting a differential scanning calorimetry (DSC) profile having an endothermic melting peak with onset at 43° C. and peak maximum at 44° C., further optionally with a melting enthalpy of 66 J/g.

Figure 1:
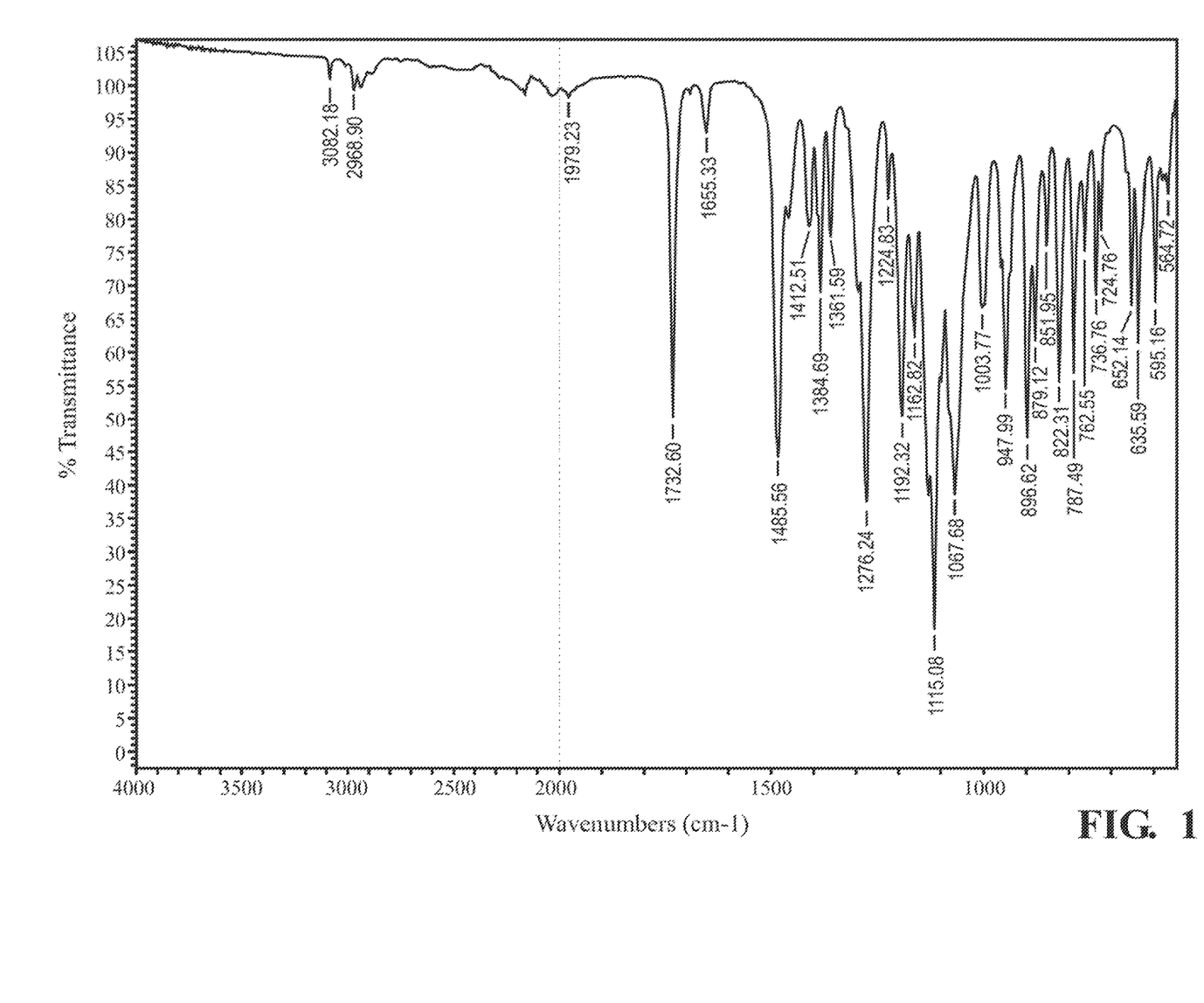
FIG. 1 is a an infrared (IR) spectrograph of crystalline modification I of tefluthrin.
Figure 2:
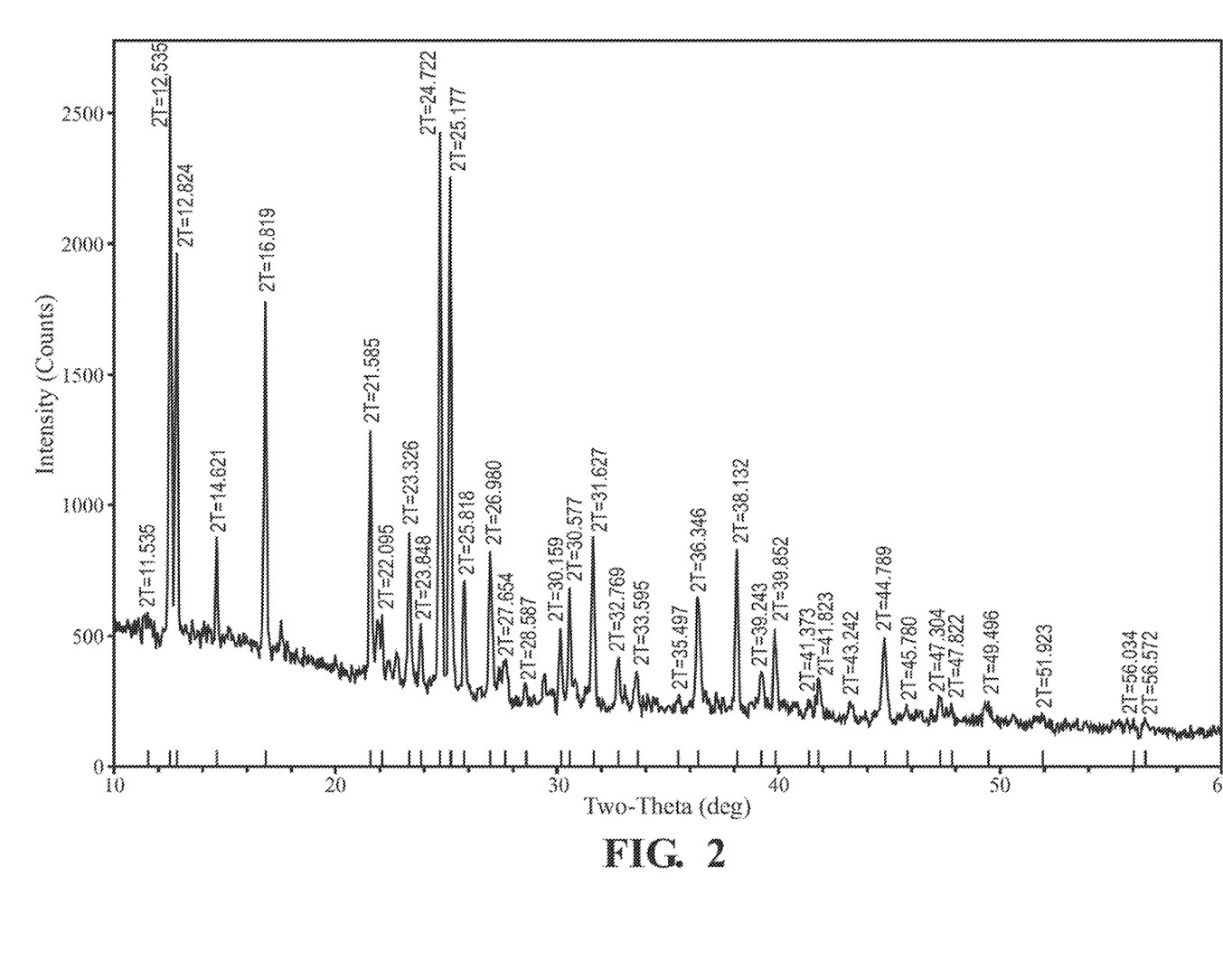
FIG. 2 is an X-ray powder diffractogram of crystalline modification I of tefluthrin.
Figure 3:
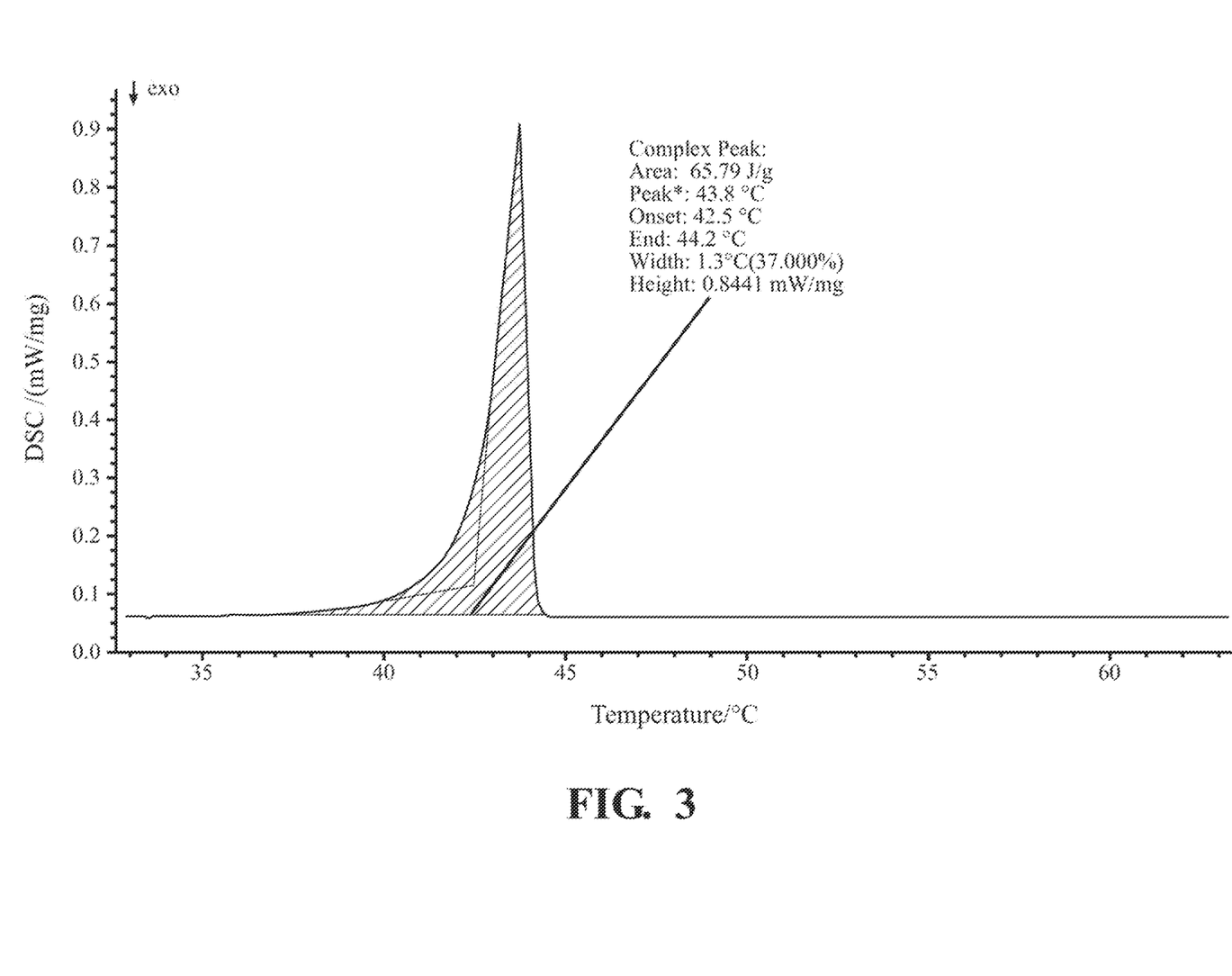
FIG. 3 is a Differential Scanning Calorimetry (DSC) thermogram of crystal modification I of tefluthrin.

In a fifth aspect, the present invention provides a crystalline modification I of tefluthrin, optionally according to any one of the first to fourth aspects of the invention, characterized by X-ray powder diffraction pattern substantially as shown in FIG. 2, and/or characterized by an IR spectrum substantially as shown in FIG. 1, and/or characterized by a DSC thermogram substantially as shown in FIG. 3.

In a sixth aspect, the present invention provides a crystalline modification I of tefluthrin, optionally according to any one of the first to fifth aspects of the invention, obtainable by the process substantially as described in Example 2 or 3.

In a seventh aspect, the present invention provides a crystalline modification I of tefluthrin, optionally according to any one of the first to sixth aspects of the invention, obtainable by the process of the eighth aspect of the invention.

It has been found that the present crystalline modification I of tefluthrin has a significant reduction in its toxicity, which may significantly reduce the toxicity problem encountered in current commercially available formulations. In addition, it has been found that the crystalline modification I of tefluthrin is easier to comminute or grind compared to amorphous tefluthrin prepared in accordance with the disclosure of U.S. Pat. No. 4,405,640. This allows the preparation of commercial formulations such as granules (GR), suspension concentrates (SC), oil-based suspension concentrates (OD), water-dispersible granules (WG) and water-soluble granules (SG).

By virtue of its low toxicity, the crystalline modification I of tefluthrin may be highly suitable for preparing compositions for controlling undesirable insects.

In an eighth aspect, the present invention provides a process for preparing a crystalline modification I of tefluthrin comprising the steps of:
  i) dissolving tefluthrin in a solvent or mixture of solvents;
  ii) precipitating the dissolved tefluthrin into the crystalline modification I of tefluthrin; and
  iii) isolating the precipitated crystalline modification I.

In an embodiment of the eighth aspect of the invention, the tefluthrin in step i) is amorphous tefluthrin.

Methods for preparing amorphous tefluthrin are well known in the art, and amorphous tefluthrin is manufactured and available on a commercial scale. A particularly suitable method for preparing amorphous tefluthrin is described in U.S. Pat. No. 4,405,640.

In an embodiment of the eighth aspect of the invention, the solvent is selected from halogenated hydrocarbons (for example, 2-butanone, dimethoxyethane, trifluoro methyl benzene, chlorobenzene, bromobenzene, dichlorobenzene, chlorotoluene and trichlorobenzene), ethers (for example, ethyl propyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyl-tetrahydrofuran, polyethers of ethylene oxide and/or propylene oxide), nitrated hydrocarbons (for example, nitromethane, nitroethane, nitropropane, nitrobenzene, chloronitrobenzene and o-nitrotoluene), aliphatic, cycloaliphatic or aromatic hydrocarbons (for example, pentane, n-hexane, n-heptane, n-octane, nonane, ethyl benzene, mesitylene), cymene, petroleum fractions having a boiling range of from 70° C. to 190° C., cyclohexane, methylcyclohexane, petroleum ether, ligroin, octane, benzene, esters (for example, malonates, acetic acid n-butyl ester (n-butyl acetate), methyl acetate, ethyl acetate, isobutyl acetate, dimethyl carbonate, diethyl carbonate, dibutyl carbonate and ethylene carbonate), methyl ethyl ketone, 2-butanone and aliphatic alcohols (for example, methanol, isopropyl alcohol, ethanol, n-propanol, isopropanol, n-butanol and tert-amyl alcohol) and mixtures thereof. Solvent mixtures of more than 2, or 3 or 4 components are also envisaged by embodiments of the invention.

In an embodiment of the eighth aspect of the invention, the solvent is selected from the group consisting of diethyl ether, 2-butanone, dimethoxyethane, chlorobenzene, dichlorobenzene, ethyl benzene, trifluoro methyl benzene, mesitylene, nitrobenzene, methyl ethyl ketone, ethanol, isopropanol, or mixture of THF-hexane, THF-water, or mixtures thereof.

In an embodiment of the eighth aspect of the invention, the solvent is selected from the group consisting of 2-butanone or dimethoxyethane or a mixture thereof.

According to an embodiment of the eighth aspect of the present invention, the crystalline modification I of tefluthrin is prepared by dissolving amorphous tefluthrin in a solvent or a solvent mixture as a concentrated solution by heating from ambient temperature to a temperature at or below the reflux temperature of the solvent or the solvent mixture. Optionally, the concentrated solutions can be prepared at the reflux temperature of the solvents. The concentration of the solution depends on the solubility of tefluthrin in the corresponding solvent or solvent mixture.

In an embodiment of the eighth aspect of the invention, the concentrated homogeneous solution thus prepared as in step (i) is then cooled to a temperature of about 0° C. to 20° C. to crystallize the desired crystalline form from the solvent. The crystalline modification I of tefluthrin can also be crystallized out by concentrating the homogeneous solution by removing the solvent or solvent mixture to a certain volume with or without applying vacuum and cooling to below the reflux temperature of the solvent or the solvent mixture.

In an embodiment of the eighth aspect of the invention, the crystalline modification I of tefluthrin can also be effected by adding seed crystals of the desired crystalline form during crystallization into a solution prepared in step (i), which can promote or accelerate the crystallization.

The seed crystal amount added to the concentrated solution is typically in the range of 0.001% to 10% by weight, preferably 0.001% to 2.5% by weight, and more preferably 0.005 to 0.5% by weight based on the weight of tefluthrin used for the preparation of concentrated solution in step (i). Optionally, the seed crystals are added to the concentrated solution at the temperature below the boiling point of the corresponding solvent or the solvent mixture.

In an embodiment of the eighth aspect of the invention, the precipitated crystalline modification I of tefluthrin obtained from step (ii) is isolated by the usual solid component separating techniques from solutions, such as filtration, centrifugation or decantation. Then, the isolated solid will be washed with solvent one or more times. Optionally, the solvent employed in the washing stage consists of one or more components of the solvent or solvent mixture employed for the preparation of concentrated solution in step (i), as described 2-butanone, and dimethoxyethane are particularly suitable solvents for washing the recovered solid of tefluthrin. The washing is usually carried out using the corresponding solvent or solvent mixture between room temperature and 0° C., depending on the solubility of the crystal in order to avoid the loss of crystal as far as possible in the corresponding washing solvent.

In an embodiment of the eighth aspect of the invention, the crystalline modification I of tefluthrin is dissolved and recrystallized. The washings and/or the solvent of crystallization in any of the methods may be concentrated to obtain solid tefluthrin which may be recycled.

In a ninth aspect, the present invention provides a crystalline modification I of tefluthrin obtained according to the eighth aspect of the invention, having a crystalline tefluthrin content of at least 98% by weight.

In a tenth aspect, the present invention provides a composition comprising the crystalline modification I of tefluthrin according to any one of the first to seventh and ninth aspects of the invention, and at least one auxiliary.

In an eleventh aspect, the present invention provides a use of the crystalline modification I of tefluthrin according to any one of the first to seventh and ninth aspects of the invention, or a composition according to the tenth aspect of the invention for control of insects.

In an embodiment of the tenth aspect of the invention, the amount of the crystalline modification I of tefluthrin is less than 50% by weight of the composition, preferably less than 30% by weight of the composition, still more preferably about 3% by weight of the composition.

The use of amorphous tefluthrin as an insecticide is well known in the art and is used on a commercial scale. It has been found that the crystalline modification I of tefluthrin is also active in controlling insects. As a result, the techniques of formulating and applying tefluthrin known in the prior art documents described hereinbefore, can also be applied in an analogous manner to tefluthrin in the crystalline modification I. Accordingly, the present invention provides an insecticidal composition comprising tefluthrin in the crystalline modification I as defined hereinbefore.

The invention furthermore provides processes for preparing compositions for controlling insect using the crystalline modification I of tefluthrin.

The invention also provides a method for controlling insects, comprising applying to the plant, plant part, or surroundings of the plant, an effective amount of crystalline modification I of tefluthrin according to any one of the first to seventh and ninth aspects of the invention, or a composition according to the tenth aspect of the invention. Accordingly, this provides for controlling insects in plants, plant parts, and/or their surroundings, comprising applying to the foliage or fruit of the plant, plant part, or surroundings of the plant, an effective amount of crystalline modification I of tefluthrin.

In an embodiment of the tenth aspect of the invention, the composition is in the form of a suspension concentrate (SC), an oil-based suspension concentrate (OD), a water-soluble granule (SG), a dispersible concentrate (DC), an emulsifiable concentrate (EC), an emulsion seed dressing, a suspension seed dressing, a granule (GR), a microgranule (MG), a suspoemulsion (SE) and a water-dispersible granule (WG). The crystalline modification I of tefluthrin can be included into these customary formulations in a known manner using suitable auxiliaries, carriers and solvents and the like.

In an embodiment of the tenth aspect of the invention, the composition is in the form of a granule (GR).

In an embodiment of the tenth aspect of the invention, the crystalline modification I of tefluthrin may be present in a concentration sufficient to achieve the required dosage when applied to plants or the loci thereof, desirably in a concentration of from about 0.1 to about 50% by weight of the total mixture.

These formulations are prepared in a known manner by mixing the crystalline modification I of tefluthrin with at least one auxiliary, for example, carriers, surfactants, diluents, wetting agents, dispersing agents and any necessary adjuvants and other formulation ingredients.

The carrier may be precipitated silica, colloidal silica, attapulgite china clay, talc, kaolin or a combination thereof, preferably precipitated silica and kaolin.

The diluents include, but are not limited to, lactose, glucose, fructose, maltose, sucrose, in the anhydrous or hydrate forms, urea, water-soluble or dispersible polymers, water soluble inorganic salts or a combination thereof. Lactose, starch or combinations thereof are particularly useful for the composition of the invention.

Wetting agents include, but are not limited to, alkyl sulfosuccinates, laureates, alkyl sulfates, phosphate esters, acetylenic diols, ethoxyfluornated alcohols, ethoxylated silicones, alkyl phenol ethyoxylates, benzene sulfonates, alkyl-substituted benzene sulfonates, alkyl a-olefin sulfonates, naphthalene sulfonates, alkyl-substituted napthalene sulfonates, condensates of naphthalene sulfonates and alkyl-substituted naphthalene sulfonates with formaldehyde, and alcohol ethoxylates. Sodium alkylnaphthalenesulfonate blend (Morwet-EFW) are particularly useful for the composition of the invention Dispersing agents include, but are not limited to, sodium, calcium and ammonium salts of ligninsulfonates (optionally polyethoxylated); sodium and ammonium salts of maleic anhydride copolymers; sodium salts of condensed phenolsulfonic acid; modified styrene acrylic polymer and naphthalene sulfonate-formaldehyde condensates. Of note are compositions comprising up to 10% by weight of dispersant. Modified styrene acrylic polymer (Atlox Metasperse 550S) are particularly useful for the composition of the invention.

In an embodiment of the tenth aspect of the invention, the crystalline modification I of tefluthrin according to the invention can be present in its commercially available formulations and in its use forms, prepared from these formulations, and as a mixture with other active compounds such as insecticides, attractants, sterilizing agents, bactericides, acaricides, nematicides, fungicides, growth-regulating substances, herbicides, safeners, fertilizers and semiochemicals or with agents for improving plant properties.

In an embodiment of the tenth aspect of the invention, the crystalline modification I of tefluthrin can furthermore be present in formulations and its use forms, prepared from these formulations, and as a mixture with inhibitors which reduce degradation of the active compounds after their use in the environment of the plant, on the surface of plant parts or in plant tissues.

All plants and plant parts can be treated in accordance with the invention. In the present context, plants are to be understood as meaning all plants and plant populations such as desired and undesired wild plants or crop plants (including naturally occurring crop plants). Crop plants can be plants which can be obtained by conventional breeding and optimization methods, by biotechnological and genetic engineering methods, or by combinations of these methods, including the transgenic plants and the plant cultivars which can or cannot be protected by plant breeders' rights. Plant parts are to be understood as meaning all parts and organs of plants above and below the ground, such as shoot, leaves, needles, stalks, stems, flowers, fruit bodies, fruits, seeds, roots, tubers and rhizomes. Harvested materials, and vegetative and generative propagation materials, for example, cutting, tubers, meristem tissue, rhizomes, offsets, seeds, single and multiple plant cells and any other plant tissues, are also included.

As used herein, the term "about," when used in connection with a numerical amount or range, means somewhat more or somewhat less than the stated numerical amount or range, to a deviation of ±10% of the stated numerical amount or endpoint of the range.

"Surrounding," as used herein, refers to the place on which the plants are growing, the place on which the plant propagation materials of the plants are sown or the place on which the plant propagation materials of the plants will be sown.

"Precipitation" as used herein, refers to the sedimentation of a solid material (a precipitate), including the sedimentation of a crystalline material, from a liquid solution in which the solid material is present in amounts greater than its solubility in the amount of liquid solution.

Treatment according to the invention of the plants and plant parts with the compositions or formulations of the inventions is carried out directly or by allowing the compositions or formulations to act on their surroundings, habitat or storage space by the customary treatment methods. Examples of these customary treatment methods include dipping, spraying, vaporizing, fogging, broadcasting, painting on in the case of propagation material, and applying one or more coats particularly in the case of seed.

The benefits of the present invention are seen most when the insecticidal composition is applied to kill insects, such as Cutworm, Lesser Cornstalk Borer, Mexican Corn Rootworm, Northern Corn Rootworm, Seedcorn Beetle, Seedcorn Maggot, Southern Corn Rootworm, Western Corn Rootworm, White Grub and Wireworm in growing crops of useful plants: such as maize, sugar beet, potatoes and vegetables. In this invention, treatment of maize is particular beneficial.

Throughout the description and claims of this specification, the words "comprise" and variations of the words, for example "comprising" and "comprises", mean "including but not limited to", and do not exclude other moieties, additives, components, integers or steps. Moreover the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects. Other features of the invention will become apparent from the following examples. Generally speaking the invention extends to any novel one, or any novel combination, of the features disclosed in this specification (including any accompanying claims and drawings). Thus features, integers, characteristics, compounds, chemical moieties or groups described in conjunction with a particular aspect, embodiment or example of the invention are to be understood to be applicable to any other aspect, embodiment or example described herein unless incompatible therewith. Moreover unless stated otherwise, any feature disclosed herein may be replaced by an alternative feature serving the same or a similar purpose.

Where upper and lower limits are quoted for a property then a range of values defined by a combination of any of the upper limits with any of the lower limits may also be implied.

In this specification, references to properties are—unless stated otherwise—to properties measured under ambient conditions, i.e. at atmospheric pressure and at a temperature of about 20° C.

The term "crystalline", as used herein, refers to a solid state form wherein molecules are arranged to form a crystal lattice comprising distinguishable unit cells. In general, crystalline material may, for example, be identified by yielding diffraction peaks when subjected to X-ray radiation and/or exhibiting an endothermic melting peak profile with a characteristic sharp peak under differential scanning calorimetry (DSC).

All percentages are given in weight % unless otherwise indicated.

As used herein, a phrase referring to "at least one of" a list of items refers to any combination of those items, including single members. As an example, "at least one of: a, b, or c" is intended to cover: a, b, c, a-b, a-c, b-c, and a-b-c.

The reference to any prior art in this specification is not, and should not be taken as, an acknowledgement of any form of suggestion that such prior art forms part of the common general knowledge.

BRIEF DESCRIPTION OF DRAWINGS

The invention can be more clearly understood by reference to the drawings, which are described below, and are intended to exemplify and illustrate, but not to limit, the scope of the invention, wherein.

DETAILED DESCRIPTION

The present invention will now be described by the following examples, and in which the following measurement techniques have been employed, and which the examples are provided for illustrative purposes only, and not intended to limit the scope of the disclosure.

All X-ray diffractograms were determined using powder diffractometer in reflection geometry at 25° C., using the following acquisition parameters:

X'Pert Pro MPD from PANalytical B.V.
Theta compensating slit and graphite monochromator
Copper (K-alpha) radiation, 40 kV, 40 mA
Step size: 0.03 degree 2-theta
Count time: 1.0 second
Maximum peak intensity: 1705 counts per second
Scan range: 3-60 degrees 2-theta The IR spectrum was measured with the resolution of 4 $cm^{-1}$ and with the number of scans of 16 for the crystallized samples. The crystalline modification I of oxamyl can be identified by its characteristic functional group vibration peaks at wavenumbers ($cm^{-1}$, ±0.2%) of one or more of 3082.18, 1732.60, 1655.33, 1485.56, 1384.69, 1361.59, 1276.24, 1115.08, 1162, and 1067.68 $cm^{-1}$ as shown in FIG. 1.

All IR spectra were obtained using the following acquisition parameters:

| | |
|---|---|
| FT-IR spectrometer | Nicolet ™ iS 5 |
| Diamond ATR unit | Thermo Scientific ™ iD5 ATR |
| Wavelength range | 550-4000 cm$^{-1}$ |
| Resolution | 4 cm$^{-1}$ |
| Number of scans | 16 |

All DSC thermograms were obtained using the following acquisition parameters:

| | |
|---|---|
| Differential Scanning Calorimeter | DSC 214 Polyma from NETZSCH-Geratebau GmbH |
| Range | 60° C./1.0(K/min)/160° C. |
| Sample car./TC | DSC 214 Corona sensor/E |
| Segments | 1/1 |
| Crucible | Pan Al, closed |
| Atmosphere | $N_2$, 50.0 ml/min/$N_2$, 70.0 ml/min |
| Corr/m. range | 000/5000 μV |

EXAMPLES

Example 1: Preparation of Amorphous Tefluthrin in Accordance with the Disclosure of U.S. Pat. No. 4,405,640 Example 2+Example 3(a) (i)

(a) Preparation of 2,3,5,6-tetrafluorotoluene

A solution of n-butyllithium in hexane (1.6 M, 62.5 ml) was added dropwise to a well stirred solution of 1,2,4,5-tetrafluorobenzene (15.0 g) in dry tetrahydrofuran (150 ml) maintained at a temperature of −60° C. under an atmosphere of dry argon. When the addition was complete, the mixture was stirred at −45° C. for 2 hours and then methyl iodide (14.2 g) was added dropwise whilst the temperature was kept at −45° C. After a period of 30 minutes the mixture was allowed to warm to the ambient temperature, poured into distilled water and the mixture extracted with diethyl ether (2×50 ml), and the extracts dried over anhydrous magnesium sulphate. After filtering the solution was concentrated by evaporation of the solvents at atmospheric pressure. The residual oil was distilled and the fraction boiling point is in the range 115° C.-122° C. at atmospheric pressure. (6.2 g) was collected, and identified by Nuclear magnetic resonance spectroscopy (n.m.r.) and gas chromatographic analysis as consisting of ca. 90% of the required 2,3,5,6-tetrafluorotoluene and ca. 10% of 2,3,5,6-tetrafluoroxylene.

(b) Preparation of 4-methyl-2,3,5,6-tetrafluorobenzoic acid

The product of step (a) above (5.5 g) was mixed with diethyl ether (35 ml), the mixture was cooled to −70° C., and maintained at this temperature whilst a solution of n-butyllithium in h-hexane (1.6 M, 21 ml) was slowly added. The mixture was stirred for a period of 1 hour during which time a fine white precipitate was formed. Dry carbon dioxide gas was then passed into the mixture for 30 minutes whilst the temperature was maintained within the range −70° C. to −40° C. Then dry carbon dioxide gas was continued to be passed in thereafter whilst the mixture was allowed to warm to the ambient temperature. After acidifying with dilute hydrochloric acid (6 N, 40 ml) the organic phase was separated, washed with water and dried over anhydrous magnesium sulphate. After evaporation of the solvents under reduced pressure, the residual oil (which from n.m.r. analysis was shown to be an approximately 1:1 mixture of the desired product and pentanoic acid) was carefully distilled under reduced pressure (water pump) using a Kugelrohr apparatus, and the fraction which solidified on cooling was collected and precipitated from toluene.

(c) Preparation of 4-methyl-2,3,5,6-tetrafluorobenzyl alcohol 4-methyl-2,3,5,6-tetrafluorobenzoic acid (500 mg) was dissolved in dry diethyl ether (5.0 ml) and added dropwise to a suspension of lithium aluminum hydride (100 mg) in dry ether (10 ml) under an argon atmosphere at the ambient temperature. When the addition was complete and the effervescence had subsided the mixture was heated at the reflux temperature for a period of 1 hour. After allowing the mixture to cool to the ambient temperature, water (10 ml) was cautiously added and the resultant mixture was extracted with diethyl ether (2×20 ml), the extracts washed with water and dried over anhydrous magnesium sulphate. After filtration the filtrate was concentrated by evaporation of the solvent. The residual low melting solid was recrystallised from petroleum ether (boiling range 40° C.-60° C.) to yield 4-methyl-2,3,5,6-tetrafluorobenzyl alcohol (200 mg).

Example 13+Example 14 (Product A)

A mixture of thionyl chloride (5.0 ml) and 3-(2-chloro-3,3,3-trifluoroprop-1-en-yl)-2,2-dimethylcyclopropane carboxylic acid (50% cis, 50% trans (w/w), 0.242 g) was heated at the reflux temperature for 5 hours, and then kept at the ambient temperature for 16 hours. After removing the excess thionyl chloride by evaporation under reduced pressure (the last traces being removed by azeotropic distillation with toluene) the resultant acid chloride was added to a mixture of 4-methyl-2,3,5,6-tetrafluorobenzyl alcohol (0.24 g), dry pyridine (0.08 g) and dry toluene (10 ml), and the resultant mixture stirred at the ambient temperatures for 2 hours and then stood at the ambient temperature for a further 16 hours. After adding toluene (10 ml) the mixture was washed successively with dilute hydrochloric acid (2 N, 20 ml), water and saturated sodium bicarbonate solution, dried over anhydrous magnesium sulphate and concentrated by evaporation of the solvent under reduced pressure yielding tefluthrin.

Whole Scheme:

Scheme 1. Synthesis of tefluthrin

Figure 4:
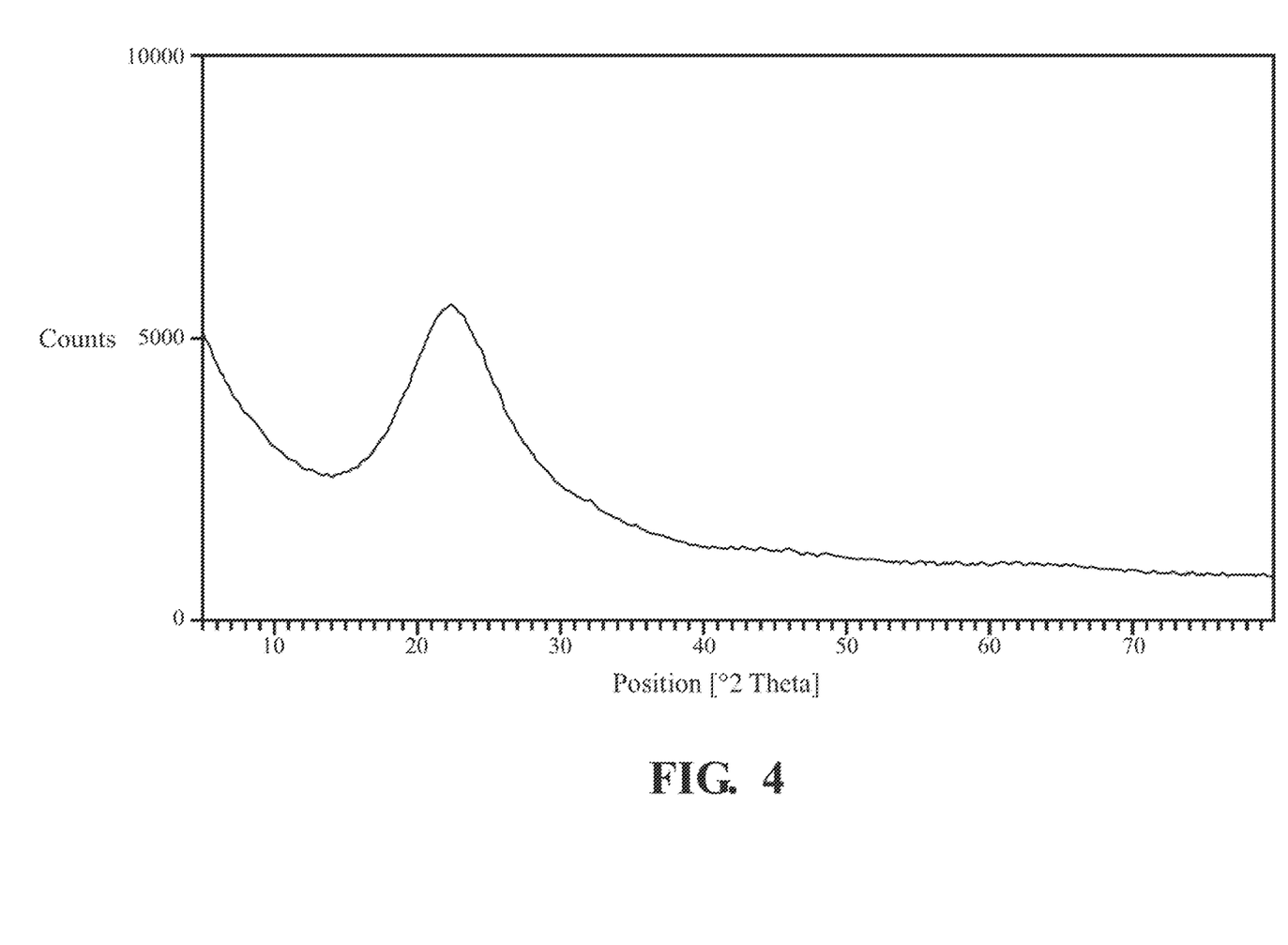
FIG. 4 is an X-ray powder diffractogram of amorphous tefluthrin.

As shown in FIG. 4, the X-ray powder diffraction pattern of the resulting tefluthrin product has no significant signals, which indicates the tefluthrin product prepared in accordance with the disclosure of U.S. Pat. No. 4,405,640 is amorphous.

Example 2: Preparation of the Crystalline Modification I of Tefluthrin

Crystallization from Dimethoxyethane

Amorphous tefluthrin sample (10 g) prepared in Example 1 was taken in a 3-neck round bottom flask along with dimethoxyethane (60 mL) and the resulting slurry was heated to 70° C. to get a homogeneous solution. The homogeneous solution was stirred at 70° C. for 2 h and the insoluble particles, if any, were filtered and the solution was slowly cooled to 20° C.-25° C. Upon cooling, fine crystals were formed and the resulting heterogeneous mixture was stirred at 20° C. for 2 h. Then, the slurry was filtered and washed with dimethoxyethane (6 mL). The filtered crystals were dried under vacuum at 20° C. The crystalline product obtained had a purity of about 98% and the recovered yield as crystal was found to be about 85%.

The obtained crystal was analyzed by IR spectrometry, X-RPD, and DSC and found to be a crystalline modification I of tefluthrin as shown in FIGS. 1, 2 and 3, respectively.

The IR spectrum of the crystalline modification I of tefluthrin is shown in FIG. 1. The IR spectrum of tefluthrin exhibited the functional group characteristic vibrations peaks at wavenumbers (cm$^{-1}$, ±0.2%) of one or more of 3082.18, 1732.60, 1655.33, 1485.56, 1384.69, 1361.59, 1276.24, 1115.08, 1162, and 1067.68 cm$^{-1}$.

The DSC thermogram of tefluthrin exhibited an endothermic melting peak with onset at 42.5° C., and a peak maximum at 43.8° C., and a melting enthalpy of 65.79 J/g as shown in FIG. 3.

The X-ray powder diffractogram of crystals exhibited the reflexes in FIG. 2 and the values are summarized in Table 1.

TABLE 1

| Crystalline Modification | |
|---|---|
| 2θ (°) | d (Å) |
| 12.535 ± 0.200 | 8.19 ± 0.05 |
| 12.824 ± 0.200 | 8.01 ± 0.05 |
| 16.819 ± 0.200 | 6.12 ± 0.05 |
| 21.585 ± 0.200 | 4.78 ± 0.05 |
| 22.095 ± 0.200 | 4.67 ± 0.05 |
| 23.326 ± 0.200 | 4.42 ± 0.05 |
| 24.722 ± 0.200 | 4.18 ± 0.05 |
| 25.177 ± 0.200 | 4.10 ± 0.05 |
| 25.818 ± 0.200 | 4.00 ± 0.05 |
| 26.980 ± 0.200 | 3.83 ± 0.05 |
| 27.654 ± 0.200 | 3.74 ± 0.05 |
| 30.577 ± 0.200 | 3.39 ± 0.05 |
| 31.627 ± 0.200 | 3.28 ± 0.05 |

Example 3: Preparation of the Crystalline Modification I of Tefluthrin

Crystallization from 2-butanone

Amorphous tefluthrin (5 g) sample prepared in Example 1 was taken in a 3 neck round bottom flask along with 1,2-dichloroethane (35 mL) and the resulting slurry was heated to 70° C. to get a homogeneous solution. The resultant hot solution was stirred at 70° C. for 2 h and the insoluble particles, if any, were filtered and the solution was slowly cooled to 20° C.-25° C. The desired crystalline product was precipitated out as fine crystal during cooling and the mixture was stirred at 20° C. for 2 h. Then, the slurry was filtered and washed with 2-butanone (6 mL). The filtered crystals were dried under vacuum at 20° C. The crystal obtained had a purity of about 98% and the recovered yield as crystal was found to be about 85%.

The crystals were characterized as being the crystalline modification I of tefluthrin using IR spectrometry, X-ray powder diffraction and DSC as described in Example 2.

Formulation Examples

Example 4: Preparation of 3% Granule (GR) of Tefluthrin 3.06 g of tefluthrin was mixed with 4.00 g of precipitated silica, then ground and blended to form a first mixture; thereafter added 11.94 g of Atlox Metasperse 550 S and 6.0 g of Morwet-EFW to the first mixture to form a second mixture; then 30.0 g of Lactose and 45.0 g of Kaolin were mixed with the second mixture to form a third mixture; milled the third mixture until the particles are 75 microns or less in size, preferably D100≤30; and D90≤15 μm; added 12.28 g water to wet the milled third mixture; extruded the wet milled third mixture to form granules; and dried the granules below the melting point of the pesticide to produce the agricultural pesticide formulation.

TABLE 2

| Content | Weight % | | Function |
|---|---|---|---|
| Amorphous tefluthrin, 98% (prepared in example 1) | 3.06 | 0 | Active ingredient |
| Tefluthrin, crystalline modification I, 98% (prepared in Example 2) | 0 | 3.06 | Active ingredient |
| Precipitated silica | 4 | 4 | Carrier |
| Modified styrene acrylic polymer (Atlox Metasperse 550S) | 11.94 | 11.94 | Dispersing agent |
| Sodium alkylnaphthalenesulfonate blend (Morwet-EFW) | 6 | 6 | Wetting agent |
| Lactose | 30 | 30 | Diluent |
| Kaolin | 45 | 45 | Diluent |

Example 5: Preparation of 5% Granule (GR) of Tefluthrin 5.10 g of tefluthrin was mixed with 4.00 g of precipitated silica, then ground and blended them to form a first mixture; thereafter added 9.90 g of Atlox Metasperse 550S and 6.0 g of Morwet-EFW to the first mixture to form a second mixture; then 30.0 g of Lactose and 45.0 g of Kaolin were mixed with the second mixture to form a third mixture; milling the third mixture until the particles are 75 microns or less in size preferably D100≤30; and D90≤15 μm; adding 12.28 g water to wet the milled third mixture; extruded the wet milled third mixture to form granules; and dried the granules below the melting point of the pesticide to produce the agricultural pesticide formulation.

TABLE 3

| Content | Weight % | | Function |
|---|---|---|---|
| Amorphous tefluthrin, 98% (prepared in example 1) | 5.10 | 0 | Active ingredient |
| Tefluthrin, crystalline modification I, 98% (prepared in Example 2) | 0 | 5.10 | Active ingredient |
| Precipitated silica | 4 | 4 | Carrier |
| Modified styrene acrylic polymer (Atlox Metasperse 550S) | 9.9 | 9.9 | Dispersing agent |
| Sodium alkylnaphthalenesulfonate blend (Morwet-EFW) | 6 | 6 | Wetting agent |
| Lactose | 30 | 30 | Diluent |
| Kaolin | 45 | 45 | Diluent |

Example 6: Toxicity Test

Sample Preparation

Samples prepared in Examples 4 and 5 were used to prepare stock solutions (1 g/L) in dimethyl sulphoxide (DMSO). Serial dilutions of the stock solutions were prepared in DMSO. The final concentration was 0.5 mole/L. Concentrations are presented as nominal values.

Marine Copepod Culture Preparation

Copepod (A clausi) was held into culture vessels (2.5 L plastic buckets) and maintained at 14±1° C. in a temperature-controlled room under dim light, with a photoperiod of 14 hours light and 10 hours dark.

Acute Toxicity Test

The acute toxicity of tefluthrin in its different formulation prepared in Examples 4 and 5 to marine copepods were investigated in 48-h static renewal tests using adult stages of marine copepods. Adult copepod was exposed in a series of tests to five toxicant concentrations, a control and with three replicates of 10 animals per concentration. Animals were transferred into test solutions using disposable Pasteur pipettes in a minimum of sea water to reduce dilution. Exposure vessels were 50 mL borosilicate glass beakers containing 40 mL of test solution. Tests were undertaken in a temperature-controlled room (14° C.±1° C.) under dim fluorescent light with a photoperiod of 14 hours light and 10 hours dark. The test end point was immobility, identified by a lack of movement when gently prodded or blown with a stream of water. Animals were checked for mobility after 48 hours by observation under a stereo microscope. Tests were considered successful if control survival was greater than 90%.

Acute LC50 values were calculated using probit or Spearman-Karber analyses using Tox Calc.

Result

TABLE 4

| Sample | LC50 (μg/L) |
|---|---|
| Example 4: Amorphous tefluthrin | 0.70 |
| Example 4: Tefluthrin, crystalline modification I | 5.40 |
| Example 5: Amorphous tefluthrin | 0.55 |
| Example 5: Tefluthrin, crystalline modification I | 3.80 |

It is surprising to find that the toxicity of crystalline modification I of tefluthrin is far lower than the amorphous form. For this reason, crystalline modification I of tefluthrin may be highly suitable for preparing commercial formulations.

The invention claimed is:

1. A crystalline modification I of 2,3,5,6-tetrafluoro-4-methylbenzyl-(1RS,3RS)-3-[(Z)-2-chloro-3,3,3-trifluoro-prop-1-enyl]-2,2-dimethylcyclopropanecarboxylate (tefluthrin) exhibiting at least 3 of the following reflexes, in any combination, as 2θ±0.20 degree in X-ray powder diffractogram (X-RPD) recorded using Cu—Kα radiation at 25° C.:

2θ=12.54±0.20,

2θ=12.82±0.20,

2θ=16.82±0.20,

2θ=24.72±0.20,

2θ=25.18±0.20, and

2θ=31.63±0.20.

2. The crystalline modification I of tefluthrin according to claim 1, exhibiting an IR spectrum with characteristic functional group vibration peaks at wavenumbers (cm$^{-1}$, ±0.2%) of one or more of about 3082, 1733, 1655, 1486, 1385, 1362, 1276, 1115, 1162, and 1068 cm$^{-1}$.

3. The crystalline modification I of tefluthrin according to claim 1, exhibiting a melting point of 41° C. to 46° C.

4. The crystalline modification I of tefluthrin according to claim 1, exhibiting a melting point of 42° C. to 45° C.

5. The crystalline modification I of tefluthrin according to claim 1, exhibiting a differential scanning calorimetry (DSC) profile having an endothermic melting peak with onset at 43° C. and peak maximum at 44° C.

6. The crystalline modification I of tefluthrin according to claim 5 exhibiting a melting enthalpy of 66 J/g.

7. A process of preparing a crystalline modification I of tefluthrin according to claim 1, comprising the steps of:
  i) dissolving tefluthrin in a solvent or mixture of solvents;
  ii) precipitating the dissolved tefluthrin into the crystalline modification I of tefluthrin; and
  iii) isolating the precipitated crystalline modification I.

8. The process according to claim 7, wherein the tefluthrin in step i) is amorphous tefluthrin.

9. The process according to claim 7, wherein the solvent is selected from the group consisting of diethyl ether, 2-butanone, dimethoxyethane, chlorobenzene, dichlorobenzene, ethyl benzene, trifluoro methyl benzene, mesitylene, nitrobenzene, methyl ethyl ketone, ethanol, isopropanol, THF-hexane, and THF-water.

10. The process according to claim 9, wherein the solvent is selected from the group consisting of dimethoxyethane and 2-butanone.

11. The process according to claim 7, wherein step ii) is effected by concentrating the solution and/or by cooling or by adding a seed crystal of the crystalline modification I.

12. The process according to claim 11, wherein step ii) is effected by cooling to about 0 to 20° C.

13. A crystalline modification I of tefluthrin obtained by a process according to claim 7, having a crystalline modification I of tefluthrin content of at least 98% by weight.

14. A composition comprising the crystalline modification I of tefluthrin according to claim 1 and at least one auxiliary.

15. The composition according to claim 14, wherein the auxiliary is selected from the group consisting of a carrier, a surfactant, a diluent, a wetting agent, and a dispersing agent.

16. The composition according to claim 15, wherein the carrier is selected from the group consisting of precipitated silica, colloidal silica, attapulgite china clay, talc, kaolin and a combinations thereof.

17. The composition according to claim 16, wherein the carrier is precipitated silica or kaolin.

18. The composition according to claim 15, wherein the surfactant is selected from the group consisting of modified styrene acrylic polymer (Atlox Metasperse 550S) and sodium alkylnaphthalenesulfonate blend (Morwet EFW).

19. The composition according to claim 15, wherein the diluent is selected from the group consisting of lactose, glucose, fructose, maltose, sucrose, in the anhydrous or hydrate forms, urea, water-soluble or dispersible polymers, water soluble inorganic salts and combinations thereof.

20. The composition according to claim 19, wherein the diluent is lactose or starch.

21. The composition according to claim 14, which is in the form a suspension concentrate (SC), an oil-based suspension concentrate (OD), a water-soluble granule (SG), a dispersible concentrate (DC), an emulsifiable concentrate (EC), an emulsion seed dressing, a suspension seed dressing, a granule (GR), a microgranule (MG), a suspoemulsion(SE) or a water-dispersible granule (WG).

22. The composition according to claim 21, which is the form of a granule (GR).

23. The composition according to claim 14, which comprises crystalline modification I of tefluthrin in an amount of less than 50% by weight of the composition.

24. The composition according to claim 14, which comprises crystalline modification I of tefluthrin in an amount of less than 30% by weight of the composition.

25. The composition according to claim 14, which comprises crystalline modification I of tefluthrin in an amount of about 3% by weight of the composition.

26. A method for the control of Cutworm, Lesser Cornstalk Borer, Mexican Corn Rootworm, Northern Corn Rootworm, Seedcorn Beetle, Seedcorn Maggot, Southern Corn Rootworm, Western Corn Rootworm, White Grub or Wireworm, comprising applying to a plant, plant part, or surroundings of the plant, an effective amount of crystalline modification I of tefluthrin according to claim 1.

27. A method of controlling insects, comprising applying to a plant, plant part, or surroundings of the plant, an effective amount of crystalline modification I of tefluthrin according to claim 1.

* * * * *